United States Patent
Lodaya

(10) Patent No.: US 7,622,610 B2
(45) Date of Patent: Nov. 24, 2009

(54) CRYSTALLINE ACAT INHIBITOR

(75) Inventor: Rita Mayur Lodaya, Northville, MI (US)

(73) Assignee: Graceway Pharmaceuticals, LLC, Bristol, TN (US)

( * ) Notice: Subject to any disclaimer, the term of this patent is extended or adjusted under 35 U.S.C. 154(b) by 577 days.

(21) Appl. No.: 11/354,486

(22) Filed: Feb. 15, 2006

(65) Prior Publication Data

US 2006/0189697 A1     Aug. 24, 2006

Related U.S. Application Data

(60) Provisional application No. 60/655,758, filed on Feb. 24, 2005.

(51) Int. Cl.
  *C07C 233/05* (2006.01)
  *A61K 31/16* (2006.01)
(52) U.S. Cl. ........................ 564/155; 514/616
(58) Field of Classification Search ................. 514/616; 564/155
  See application file for complete search history.

(56) References Cited

U.S. PATENT DOCUMENTS

| 4,299,845 A | 11/1981 | Loebenberg et al. |
| 6,133,326 A | 10/2000 | Mayne |
| 2005/0079144 A1 | 4/2005 | Kostlan et al. |

FOREIGN PATENT DOCUMENTS

| EP | 0 433 622 A2 | 6/1991 |
| WO | WO 01/56556 A2 | 8/2001 |

OTHER PUBLICATIONS

Yagyu et al., Absence of ACAT-1 Attenuates Atherosclerosis but Causes Dry Eye and Cutaneous Xanthomatosis in Mice with Congenital Hyperlipidemia, Journal of Biological Chemistry, pp. 21324-21330, vol. 275/28, Jul. 2000.
Co-pending, commonly assigned U.S. Appl. No. 10/958,306, filed Oct. 5, 2004 and published as 2005-0079144A1 on Apr. 14, 2005.

*Primary Examiner*—Shailendra Kumar
(74) *Attorney, Agent, or Firm*—McDermott Will & Emery LLP

(57) ABSTRACT

The invention is directed to the Form A polymorph of N-benzyl-N'-(2,6-diisopropyl-phenyl)-N-isopropyl-malonamide and its use as a therapeutic/cosmetic agent.

10 Claims, 3 Drawing Sheets

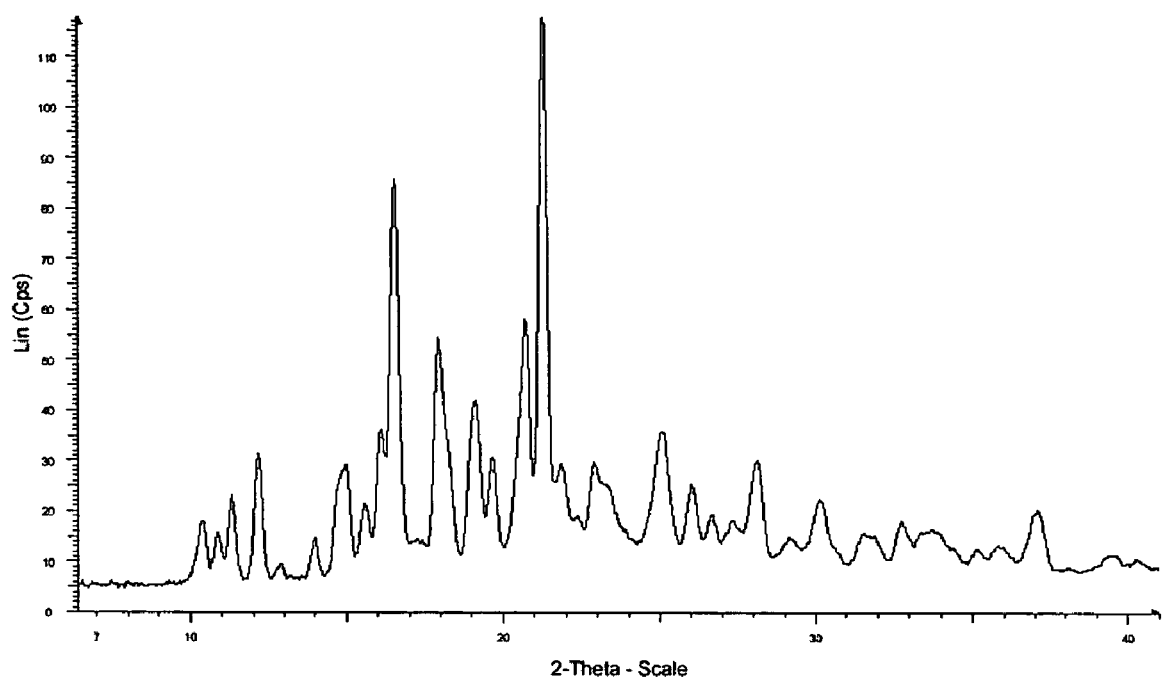
Figure 1. XRPD of Form A polymorph from Example 2 using a Bruker diffractometer

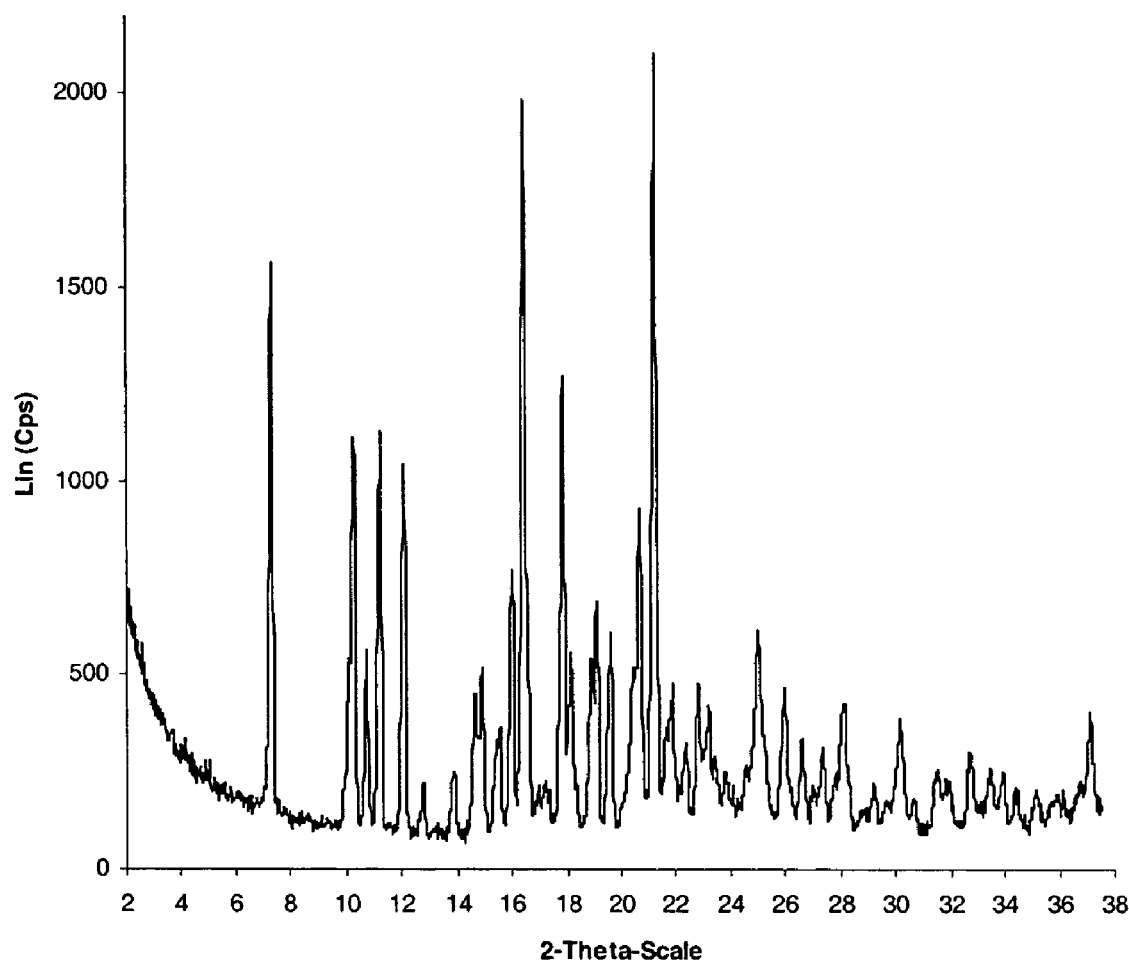
Figure 2. XRPD of Form A polymorph from Example 2 using a Scintag Diffractometer

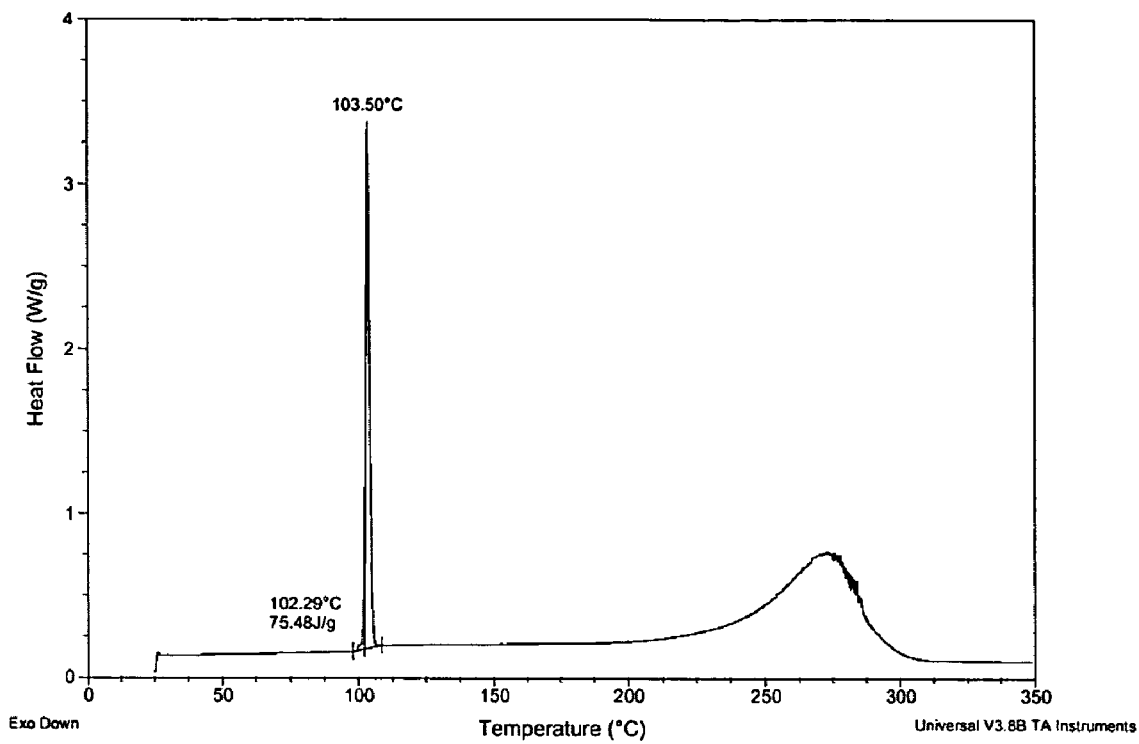
Figure 3. Thermogram of Form A Polymorph from Example 2

CRYSTALLINE ACAT INHIBITOR

CROSS REFERENCE TO RELATED APPLICATION

This application claims priority to U.S. Provisional Application Ser. No. 60/655,758 filed Feb. 24, 2005, the contents of which are hereby incorporated by reference.

FIELD OF THE INVENTION

The present invention is directed to a crystalline form of N-benzyl-N'-(2,6-diisopropyl-phenyl)-N-isopropyl-malonamide and to its use in the manufacture of medicaments.

BACKGROUND OF THE INVENTION

Human skin is composed of three primary layers, the stratum corneum, the epidermis, and the dermis. The outer layer is the stratum corneum. Its primary function is to serve as a barrier to the external environment. Lipids are secreted to the surface of the stratum corneum. These lipids decrease the stratum corneum's water permeability. Sebum typically constitutes 95% of these lipids. Abramovits et al, Dermatologic Clinics, Vol 18, Number 4, October 2000.

Sebum is produced in the sebaceous glands. These glands are present over most of the surface of the body. The highest concentration of these glands occurs on the scalp, the forehead and the face. Despite the important physiological role that sebum plays, many individuals experience excess sebum production, especially in the facial area. Excess sebum is associated with an increased incidence of acne. Even in individuals without acne, sebum can make the skin look greasy, decreasing its attractiveness. Abramovits et al, supra.

Acyl CoA cholesterol acyl transferase (ACAT) inhibitors were initially evaluated to treat elevated cholesterol. U.S. Pat. No. 6,133,326 discloses that in addition to lowering cholesterol, ACAT inhibitors reduce the secretion of sebum. Co-pending, commonly assigned, U.S. patent application Ser. No. 10/958,306 having an effective filing date of Oct. 9, 2003, discloses the use of a specific class of diamide ACAT inhibitors in the reduction of sebum. N-benzyl-N'-(2,6-diisopropyl-phenyl)-N-isopropyl-malonamide is one of the compounds whose use is exemplified in the '306 application. N-benzyl-N'-(2,6-diisopropyl-phenyl)-N-isopropyl-malonamide was initially described in European patent application 0 433 662 (see page 11, line 50, where it is referred to as N'-[2,6-bis(1-methylethyl)-phenyl]-N-(1-methylethyl)-N -(phenylmethyl) propanediamide) as an ACAT inhibitor for the treatment of elevated cholesterol. The European '662 application does not disclose the use of these compounds to control sebum secretion.

SUMMARY OF THE INVENTION

In accordance with the present invention, a crystalline form of N-benzyl-N'-(2,6-diisopropyl-phenyl)-N-isopropyl-malonamide has been discovered. The structure of N-benzyl-N'-(2,6-diisopropyl-phenyl)-N-isopropyl-malonamide is depicted below:

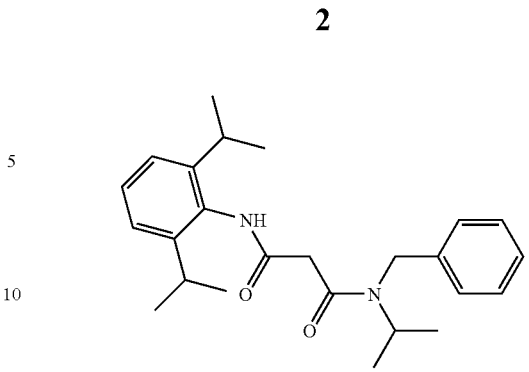

The crystalline form of N-benzyl-N'-(2,6-diisopropyl-phenyl)-N-isopropyl-malonamide is referred to as the Form A polymorph. It has a characteristic powder X-ray diffraction pattern that is described infra (XRPD).

The crystalline form may be utilized as an ACAT inhibitor. It may be administered to patients to control elevated cholesterol levels and/or to decrease sebum secretion. In a more specific embodiment, the crystalline form is incorporated into a topical dosage form that is administered to patients to decrease sebum secretion, alleviate oily skin, decrease acne, decrease shiny skin, or other cosmetic complaints typically associated with excess sebum.

In a further embodiment, the invention is directed to an article of manufacture (i.e. a kit) containing one of these topical dosage forms packaged for retail distribution, in association with instructions advising the consumer how to use the product to alleviate dermal disorders associated with excess sebum.

BRIEF DESCRIPTION OF THE DRAWINGS

FIG. 1 illustrates an X-ray powder diffraction pattern of the Form A polymorph produced in Example 2, on a scale of 6.4° 2θ to 41° 2θ.

FIG. 2 illustrates an X-ray powder diffraction pattern of the Form A polymorph, also produced in Example 2, on a scale of 2.0° 2θ to 38° 2θ, obtained with a different diffractometer.

FIG. 3 illustrates a thermogram of the Form A polymorph.

DETAILED DESCRIPTION OF THE INVENTION

A. Methods of Characterization

1) Powder X-ray Diffractometry

The experimental powder x-ray diffraction pattern depicted in FIG. 1 (i.e. XRPD) was obtained using a Bruker D8 powder diffractometer with GADDS (General Area Diffraction Detector System) C2 system with a single Goebel mirror configuration. Samples were exposed to Cu K-alpha radiation ($\lambda=0.15056$ nm) with the X-ray tube operated at 40 kV and 40 mA. Scans were run with the detector at 15.0 cm. Theta 1, or the collimator, was at 7° and Theta 2, or the detector, was at 17°. The scan axis was 2-omega with a width of 3°. At the end of each scan Theta 1 is at 10° and Theta 2 is at 14°. Samples were run for 60 seconds and scans were integrated from 6.4° to 41° 2θ. Scans were evaluated using DiffracPlus software, release 2003, with Eva version 9.0. Samples were run in ASC-6 sample holders purchased from Gem Dugout (State College, Pa.). Samples were placed in the cavity in the middle of the sample holder, and flattened with a spatula to be even with the surface of the holder. All analyses were conducted at room temperature, which is generally considered to be approximately 24° C. to 28° C.

The experimental powder x-ray diffraction pattern depicted in FIG. II (i.e. XRPD) was obtained using a Scintag X1 Advanced Diffraction System operating under Scintag DMS/NT3 1.36b software. The system uses a copper X-ray source maintained at 45 kV and 40 mA to provide CuKα$_1$ emission of 1.5406 Å and a solid-state peltier cooled detector. Beam aperture was controlled using tube divergence and anti-scatter slits of 2 and 4 mm and detector anti-scatter and receiving slits of 0.5 and 0.3 mm width. Data was collected from 2° to 38° two-theta (2θ) using a step scan of 0.03°/point and a 1 second/point counting time. Scintag round, top loading stainless steel sample cups with a 9 mm Aluminum spacer insert were utilized.

The sample was prepared by grinding a portion of sample in an agate mortar&pestle, scraping sample into the tray cavity, and flattened with the steel block to be level with the outer rim of the disk. The analysis was conducted at room temperature and atmosphere.

As is readily apparent to one skilled in the art, the results of any X-ray powder diffraction may vary and subsequent XRPD's will not be identical, even when carried out on the same lot of material. This variance can be due to test sample preparation, temperature, the particular model of X-ray diffractometer used, the operator's technique, etc. The term "approximately" if used in defining a peak in an X-ray powder diffraction pattern is defined as the stated 2θ value±0.2° 2θ. Any determination of whether a crystalline form is the Form A polymorph and encompassed by the claims should be interpreted in light of the variability in this test.

This variability is demonstrated in FIGS. 1 and 2. The same lot of N-benzyl-N'-(2,6-diisopropyl-phenyl)-N-isopropyl-malonamide was submitted to XRPD on different diffractometers by different operators. The characteristic peaks, discussed below, are present in each Figure confirming that it is the Form A polymorph. However, the relative intensity of these peaks as well as the other identifying peaks varied.

2) Differential Scanning Calorimetry

Experiments were performed using a DSC Q1000 instrument (TA Instruments, New castle, Del.). Nitrogen was used as the purge gas at a flow rate of 50 mL/min for the DSC cell and 110 mL/min for the refrigerated cooling system. The calorimeter was calibrated for temperature and cell constant using indium (melting point 156.61° C., enthalpy of fusion 28.71 J/g). Sealed aluminum pans with a pinhole were used and samples (3-5 mg) were heated at a rate of 10° C./min. Data analysis was performed using TA Instruments' Universal Analysis 2000 software for Windows Version 3.8B.

B) Form A Polymorph

As noted above, a crystalline form of N-benzyl-N'-(2,6-diisopropyl-phenyl) -N-isopropyl-malonamide has been discovered. This crystalline form is referred to herein as the Form A polymorph. The Form A polymorph can be identified by its X-ray powder diffraction pattern. A review of FIGS. 1 and 2 show that the Form A polymorph exhibits three characteristic peaks. A characteristic peak is one that exhibits a significant relative intensity in the powdered XRPD pattern and serves to distinguish crystalline forms. One occurs at approximately 28.1 degrees 2θ. A second occurs at approximately 16.0 degrees 2θ. A third peak occurs at approximately 19.6 degrees 2θ. Any one of these peaks alone, or in combination, may be used to identify the Form A polymorph.

In addition to these characteristic peaks, a review of FIGS. 1 and 2 show that other identifying peaks have also been identified. The intensity of these additional peaks can vary with the particular orientation of the polymorph sample. These additional peaks may be used to confirm the presence of the Form A polymorph, but their absence should not be used to determine that the particular material is not the Form A polymorph. These identifying peaks include: 7.3, 10.3, 10.8, 11.3, 12.1, 14.6, 14.9, 16.5, 17.9, 18.1, 18.9, 19.1, 20.7, 21.8, 22.9, 23.2, 25.0, and 26.0 (expressed in degrees 2θ, ±0.2 2θ, i.e. approximately).

The form A polymorph may also be characterized by Differential Scanning Calorimetry (DSC) as shown in FIG. 3, which shows a sharp endotherm at approximately 102° C. This corresponds to the melting of Form A polymorph. Different lots of the Form A polymorph exhibit a melting point of about 100° C.±6° C.

Thus in one embodiment the invention is directed to a crystalline polymorph of N-benzyl-N'-(2,6-diisopropyl-phenyl)-N-isopropyl-malonamide that exhibits an X-ray powder diffraction pattern having at least one characteristic peak expressed in degrees 2θ at approximately 28.1, 16.0, or 19.6. In a further embodiment, the invention is directed to a crystalline polymorph of N-benzyl-N'-(2,6-diisopropyl-phenyl)-N-isopropyl-malonamide having characteristic peaks, expressed in degrees 2θ, at approximately 28.1, 16.0, and 19.6; and which optionally exhibits at least one additional peak, expressed in degrees 2θ, at approximately 7.3, 10.3, 16.5, 17.9, 20.7, 19.1, or 25.0. In a further embodiment, the invention is directed to a crystalline polymorph of N-benzyl-N'-(2,6-diisopropyl-phenyl)-N-isopropyl-malonamide having characteristic peaks expressed in degrees 2θ at approximately 16.0, 19.6, 28.1; and which exhibits at least two additional peak, expressed in degrees 2θ, at 7.3, 10.3, 10.8, 11.3, 12.1, 14.6, 14.9, 16.5, 17.9, 18.1, 18.9, 19.1, 20.7, 21.8, 22.9, 23.2, 25.0, or 26.0.

Additionally, the invention is directed to a crystalline polymorph of N-benzyl-N'-(2,6-diisopropyl-phenyl)-N-isopropyl-malonamide having: 1) characteristic peaks expressed in degrees 2θ at approximately, 16.0, 19.6, 28.1 and 2) which exhibits at least one or two additional peaks, expressed in degrees 2θ, at approximately 7.3, 10.3, 10.8, 11.3, 12.1, 14.6, 14.9, 16.5, 17.9, 18.1, 18.9, 19.1, 20.7, 21.8, 22.9, 23.2, 25.0, or 26.0. and 3) has a melting point of 100° C.±6° C.

C) Method of Preparation

The Form A polymorph may be prepared as described in Reaction Scheme I, shown below.

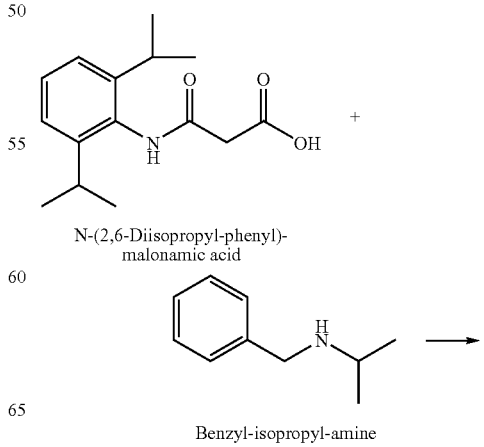

Reaction Scheme I

N-(2,6-Diisopropyl-phenyl)-malonamic acid

Benzyl-isopropyl-amine

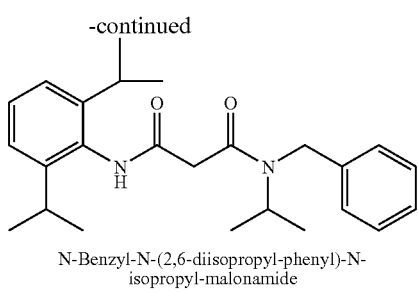

N-Benzyl-N-(2,6-diisopropyl-phenyl)-N-
isopropyl-malonamide

Recrystallization in Heptane

Form A Polymorph

One of the reactants is N-(2-6-diisopropyl-phenyl)-malonamic acid, which may be prepared as described in European Patent application 0 433 662. The other reactant is benzyl-isopropyl-amine, which may be purchased from commercial suppliers. The reaction is typically carried out by contacting equivalent amounts of the amine and the acid in an organic solvent (such as methylene dichloride) in the presence of a base (such as triethylamine) and a coupling agent such as 1-ethyl-3-(3-dimethylaminopropyl)-carbodiimide ("EDAC") or dicyclohexylcarbodiimide ("DCC"). The reactants are typically contacted at about 0° C., allowed to warm to room temperature and then stirred until the reaction is complete. Once completed, the reaction is quenched and diluted with an organic solvent. Evaporation of the solvent yields N-benzyl-N'-(2,6-diisopropyl-phenyl) -N-isopropyl-malonamide as an oil. The oil may optionally be purified by chromatography as is known in the art.

The Form A polymorph may then be obtained by subjecting the oil to recrystallization in heptane. Typically, the oil is dissolved in the heptane and stirred for an extended interval. This interval can range from 18 to 24 hours, depending upon the quantities involved. The recrystallization may be carried out at depressed temperatures, or at room temperature. If desired, seeding may be utilized to expedite the process.

D) Medical and Cosmetic Uses

Inhibition of acyl-CoA cholesterol acyl transferase (ACAT) blocks the esterification of free cholesterol-to-cholesterol esters. Cholesterol esters are the primary transportation and storage form of cholesterol in animals. In the intestines, ACAT inhibitors have been shown to inhibit the absorption of cholesterol from the gut. In the liver, inhibition of ACAT has been shown to decrease the formation and secretion of cholesterol-containing lipoproteins by decreasing the cholesterol ester mass of the lipoprotein core. For these reasons, ACAT inhibitors have previously been evaluated as a means to lower serum cholesterol levels.

Dermal sebaceous glands are holocrine glands that secrete a mixture of lipids known as sebum. Sebum is composed of triglycerides, wax, sterol esters and squalene. There is considerable variation in the composition of human sebum based on individual variables such as age, sex, diet, and disease. Sebum is produced in the acinar cells of sebaceous glands, accumulates as those cells age and migrates towards the center of the gland. At maturation, the acinar cells lyse and release sebum into the lumenal duct, from which the sebum is secreted.

Formation of sebum is regulated by a variety of hormones that act primarily to regulate the rate of lipid metabolism. Waxes and sterols are converted, within acinar cells, to a stable ester form for storage via the activity of a variety of acyl and fatty acid transferases. These esters are then stored in lipid droplets within the acinar cells prior to release.

Medicaments prepared with the Form A polymorph of N-benzyl-N'-(2,6-diisopropyl-phenyl)-N-isopropyl-malonamide (hereinafter the "compound") block the conversion of free cholesterol-to-cholesterol ester, leading to increased levels of free cholesterol within the acinar cells. While the cellular mechanism is not fully understood at the present time, the acinar cells produce less sebum when contacted with an ACAT inhibitor.

Thus, the compound inhibits the secretion of sebum and reduces the amount of sebum on the surface of the skin. The compound can be used to treat a variety of dermal diseases such as acne or seborrheic dermatitis.

In addition to treating diseases associated with excess sebum production, the compound can also be used to achieve a cosmetic effect. Some consumers believe that they are afflicted with overactive sebaceous glands. They feel that their skin is oily and thus unattractive. These individuals can utilize the compound to decrease the amount of sebum on their skin. Decreasing the secretion of sebum will alleviate oily skin in individuals afflicted with such conditions.

In order to exhibit the biological effects described above, the compound needs to be administered in a quantity sufficient to inhibit production and/or secretion of sebum by the sebaceous glands and acinar cells. This amount can vary depending upon the particular disease/condition being treated, the severity of the patient's disease/condition, the patient, the route of administration, and the presence of other underlying disease states within the patient, etc. When administered systemically, the compound typically exhibits its effect at a dosage range of from about 0.1 mg/kg/day to about 100 mg/kg/day for any of the diseases or conditions listed above. Repetitive daily administration may be desirable and will vary according to the conditions outlined above. As used in this application the term "patient" refers to a mammal, which will typically be a human.

The compound may be administered by a variety of routes. It is effective if administered orally. The compound may also be administered parenterally (i.e. subcutaneously, intravenously, intramuscularly, intraperitoneally, or intrathecally), rectally, or topically.

In a typical embodiment, the compound is utilized to prepare dosage forms that are administered topically. Topical administration is especially appropriate for acne and for cosmetic indications. The topical medicament will be applied to those areas of the skin afflicted with excess sebum production. The dose will vary, but as a general guideline, the compound will be present in a dermatologically acceptable carrier in an amount of from 0.01 to 10 w/w % and the dermatological preparation will be applied to the affected area from 1 to 4 times daily. "Dermatologically acceptable" refers to a carrier which may be applied to the skin, hair or scalp, and which will allow the drug to diffuse to the site of action. (i.e. the sebaceous glands and/or the acinar cells).

E) Cosmetic and Pharmaceutical Formulations

If desired, the compound can be administered directly without any carrier. However, to ease administration, it will typically be formulated into a pharmaceutical carrier.

For oral administration, the compound can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compound can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the compound in an aqueous or non-aqueous pharmaceutically acceptable solvent, which may also contain suspending agents, sweetening agents, flavoring agents, and preservative agents as are known in the art.

For parenteral administration the compound may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compound is being administered intrathecally, it may also be dissolved in cerebrospinal fluid as is known in the art.

Typically however, the compound will be incorporated into a formulation suitable for topical administration. Any of the topical formulations known in the art may be used. Examples of such topical formulations include lotions, sprays, creams, ointments, salves, gels, etc. Actual methods for preparing topical formulations are known or apparent to those skilled in the art, and are described in detail in Remington's Pharmaceutical Sciences, 1990 (supra); and Pharmaceutical Dosage Forms and Drug Delivery Systems, 6th ed., Williams & Wilkins (1995).

In a further embodiment, the formulations described above may be packaged for retail distribution (i.e., a kit or article of manufacture). The package will contain instructions advising the patient how to use the product to alleviate conditions such as acne, oily skin, etc. Such instructions may be printed on the box, may be a separate leaflet or printed on the side of the container holding the formulation, etc.

The compound may also be admixed with any inert carrier and utilized in laboratory assays in order to determine the concentration of the compounds within the serum, urine, etc., of the patient as is known in the art. The compound may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data are being presented in order to further illustrate the invention. This disclosure should not be construed as limiting the invention in any manner.

EXAMPLES

The following examples are presented in order to further illustrate the invention. They should not be construed as limiting the invention in any manner.

Example 1

This example illustrates the preparation of N-(2,6-Diisopropyl-phenyl)-malonamic acid, one of the starting materials for N-Benzyl-N'-(2,6-diisopropyl-phenyl)-N-isopropyl-malonamide Step A) N-(2,6-Diisopropyl-phenyl)-malonamic acid ethyl ester A 5 L 4-necked flask was fitted with a mechanical stirrer and temperature probe and then purged with nitrogen. The flask was charged with 200 mL (188 g, 1.06 mol) of 2,6-diisopropyl aniline, 163 mL (118 g, 1.17 mol) of triethylamine and 2.5 L of ethyl acetate. The clear, yellow solution was cooled to 0° C. with stirring and 143 mL (168 g, 95% pure, 1.06 mol) of ethyl malonyl chloride was added over 15 min. The internal temperature rose as high as 22° C. during the addition. The cold bath was removed and the yellow suspension was stirred for 100 min (HPLC indicated reaction completion). The suspension was filtered and the filtrate was evaporated at the Rotavap giving yellowish solids. The crude ester were then recrystallized from 3.0 L of heptane yielding 240.24 g (78%) of N-(2,6-Diisopropyl-phenyl)-malonamic acid ethyl ester as slightly yellow solids. HPLC analysis indicated >99% (a/a) purity. The materials $^1$H-NMR spectrum was consistent with structure Step B) N-(2,6-Diisopropyl-phenyl)-malonamic acid A 5 L 4-necked flask was fitted with a mechanical stirrer and charged with 240.24 g (824 mmol) of the N-(2,6-Diisopropyl-phenyl)-malonamic acid ethyl ester produced immediately above and 1200 mL of methanol. To the clear, orange solution was added 483 mL (966 mmol) of 2.0 N sodium hydroxide. The solution was stirred until HPLC analysis indicated complete reaction (ca. 2.5 h) and then acidified to pH 3 with 3N hydrochloric acid. The suspension was diluted with 2.0 L of ethyl acetate and 0.5 L of water. The aqueous layer was removed and then the organic layer was washed with 0.5 L of water and 0.5 L of brine. The aqueous layers were back-extracted with 0.5 L of ethyl acetate and the combined organic layers were then dried over magnesium sulfate. Evaporation of the solvent at the Rotavap yielded 216 g (99%) of the crude acid as yellowish solids. The crude material was slurried with 2.2 L of heptane and then isolated by filtration. The solids were washed with heptane and petroleum ether and then air-dried giving 202.53 g of the N-(2,6-Diisopropyl-phenyl)-malonamic acid as yellowish solids. HPLC analysis indicated >99% (a/a) purity. The materials $^1$H-NMR spectrum was consistent with structure.

Example 2

This example illustrates the preparation of the Form A polymorph of N-Benzyl-N'-(2,6-diisopropyl-phenyl)-N-isopropyl-malonamide A 2 liter flask equipped with a stirrer and nitrogen inlet was charged with N-( 2,6-diisopropyl-phenyl)-malonamic acid (100 g, 0.380 moles) and N-benzylisopropylamine (82 mL, 74 g, 0.5 moles). The resulting solution was stirred in an ice-acetone bath until cooled to −5° C., then EDAC (80 g, 0.42 moles) was added, followed by triethylamine (75 mL, 54 g, 0.54 moles). The mixture was stirred and allowed to come to room temperature, then left overnight. TLC (ethyl acetate: methanol, 95:5) showed unreacted acid still present. Another 8 g of EDAC and 15 mL of triethylamine were added, and the mixture was stirred at room temperature 4 h longer. TLC showed no change, and the reaction was worked up by washing, first with 2N HCl (500 mL), then 2N NaOH (acidification of the basic wash precipitated ~13 g of the unreacted malonamic acid). After the acid and base washes, the organic solution was washed with water (500 mL), then brine (250 mL). It was then dried over magnesium sulfate, filtered and concentrated to a thick oil. The crude product was taken up in a small volume of warm heptane and filtered through ~500 g of silica gel, which was rinsed with 10% ethyl acetate in heptane until all the desired product had come through. This left a thin layer of polar impurities at the top of the silica gel, and gave a nearly pure solution of the product. Most of the solvent was removed on the Rotavap, to remove the ethyl acetate, and then the oil was dissolved in warm heptane (1 liter). The solution was allowed to cool, seeded with a few crystals of the form A polymorph, and stirred at room temperature until precipitation of product was complete. The suspension was further stirred for 24 h, then chilled to 0° C. and filtered with suction. The collected product was air dried at room temperature to give 98 g of the Form A polymorph of N-benzyl-N'-(2,6-diisopropyl-phenyl)-N-isopropyl-malonamide. Melting point was 102.3° C., as determined by DSC, as described above.

Example 3

This example illustrates the preparation of the Form A polymorph of N-Benzyl-N'-(2,6-diisopropyl-phenyl)-N-isopropyl-malonamide.

N-(2,6-diisoproply-phenyl)-malonamic acid (2.759 kg, 9.88 mol) was dissolved in dichloromethane (12.5L) and the solution was cooled to −5° C. Then EDAC (2.08 kg, 10.9 mol) and triethylamine (2.05 L, 14.8 mol) were added and the mixture was stirred for 1 h at −5° C. At that temperature, N-benzylisopropylamine (2.3 L, 13.8 mol) was added and the mixture was allowed to warm up to rt overnight. IPC (HPLC) showed incomplete conversion and additional EDAC (0.378 kg, 2.0 mol) and triethylamine (0.27 L) were added and the mixture was continued to stir at rt for 3 h. Then IPC (HPLC) showed nearly complete conversion and reaction mixture was washed with 2 N HCl (15 L). The organic layer was washed with 2 N NaOH (15 L) and half saturated brine (28 L). (slow phase separation in all washings). The organic layer was separated and concentrated under reduced pressure. Heptane (12 L) was added and 10.7 L were distilled off. Ethyl acetate (2 L) was added to give a suspension. Heating to 50° C. gave a solution, which was stirred at 20° C. for over an hour. The solution was filtered through silica gel (12.2 kg), which was rinsed with ethyl acetae: Heptane 3:7 (160 L). 80 L contained the product. Samples of solutions eluted before and after the main fractions were evaporated: In the fraction before, no material was present, in the 20 L after the main fraction only 12.5 g were present. It was decided not to add this to main fraction. The solution was concentrated in the reactor at 100-150 mbar at 50° C. Heptane (28 L) was added and the suspension heated to 80° C. in order to from a solution. After stirring over the weekend, the suspension was cooled to 0° C. and stirred for further 2 h at this temperature. The suspension was filtered, washed with heptane (3 L), dried in the nitrogen steam and evaporated to dryness at the rotavap to give 1985 g of an off-white solid with a purity of 99.82% a/a by HPLC.

Example 4

This example illustrates also illustrates the preparation of the Form A polymorph of N-Benzyl-N'-(2,6-diisopropyl-phenyl)-N-isopropyl-malonamide.

A 50 gal receiver was charged with 13.2 kg (68.2 mol, 1.25 equiv.) of EDC hydrochloride and 42.5 kg of DMF ("dimethylformamide") and cooled to 0-5° C. A 100 gal reactor was charged with 14.38 kg (54.5 mol, 1.0 equiv.) of N-(2,6-diisoproply-phenyl)-malonamic acid, 3.75 kg (27.2 mol, 0.5 equiv.) of anhydrous 1-hydroxybenzotriazole and 19 kg of DMF. The mixture was cooled to 0-5° C. To this mixture was then added 9.0 kg (60.1 mol, 1.1 equiv.) of N-isopropyl benzylamine followed by a 5 kg of DMF rinse. To a 60 L stainless steel portable tank (SPAT) was pre-charged 8.5 kg (82 mol, 1.5 equiv.) of triethylamine and transferred to the reactor maintaining the temperature below 5° C. The slurry from the 50 gal receiver was then transferred to the reactor maintaining the temperature below 10° C. The mixture was heated to 20-30° C. and stirred at this temperature for 12 hours and analyzed by HPLC for the completion of reaction. The reaction mixture was diluted with 141 L of ethyl acetate and treated with 3 M hydrochloric acid, prepared by mixing 56 L of water and 22.6 kg of hydrochloric acid. The mixture was stirred well and the lower aqueous layer was separated and disposed. The ethyl acetate layer was again washed with 2 M hydrochloric acid solution prepared by mixing 73 L of water and 18.8 kg of hydrochloric acid. The organic layer was then washed with 90 L of 5% solution of sodium bicarbonate and 94 L of water. The ethyl acetate layer was then concentrated to about 90 L and transferred to a holding tank. After the tanks were cleaned and verified for final product isolation, the ethyl acetate solution of the product in the holding tank was transferred back to the reactor through an in-line filter. Distillation was continued to lower the volume to 55 L, azeotroped with 2×103 kg of heptane and concentrated to a final volume of about 132 L. The mixture was heated to 70-75° C. to dissolve the solids and slowly cooled to 15-25° C. by a series of ramps. Stirring was continued at 15-25° C. for 20 hours. The solids from an aliquot of the mixture was filtered on a glass funnel, washed with heptane and dried briefly in a vacuum oven. The slurry in the reactor was then filtered on a nutsche filter, washed with heptane and dried with 40° C. nitrogen. The product was packaged after passing through a co-mill to get 19.19 kg of the Form A polymorph.

What is claimed is:

1. Form A polymorph of N-benzyl-N'-(2,6-diisopropyl-phenyl)-N-isopropyl-malonamide.

2. A crystalline polymorph of N-benzyl-N'-(2,6-diisopropyl-phenyl)-N-isopropyl-malonamide that exhibits an X-ray powder diffraction pattern having at least one characteristic peak expressed in degrees 2θ at approximately 16.0, 19.6, or 28.1.

3. A crystalline polymorph of N-benzyl-N'-(2,6-diisopropyl-phenyl)-N-isopropyl-malonamide that exhibits an X-ray powder diffraction pattern having characteristic peaks expressed in degrees 2θ at approximately 16.0, 19.6, and 28.1.

4. The crystalline polymorph according to claim 2 which exhibits at least one additional peak, expressed in degrees 2θ, at approximately 7.3, 10.3, 16.5, 17.9, 19.1, 20.7, or 25.

5. The crystalline polymorph according to claim 3 which exhibits at least one additional peak, expressed in degrees 2θ, at approximately 7.3, 10.3, 16.5, 17.9, 19.1, 20.7, or 25.0.

6. The crystalline polymorph according to claim 2 which exhibits at least two additional peaks, expressed in degrees 2θ, at approximately 7.3, 10.3, 10.8, 11.3, 12.1, 14.6, 14.9, 16.5, 17.9, 18.1, 18.9, 19.1, 20.7, 21.8, 22.9, 23.2, 25.0, or 26.0.

7. The crystalline polymorph according to claim 3 which exhibits at least two additional peaks, expressed in degrees 2θ, at approximately 7.3, 10.3, 10.8, 11.3, 12.1, 14.6, 14.9, 16.5, 17.9, 18.1, 18.9, 19.1, 20.7, 21.8, 22.9, 23.2, 25.0, or 26.0.

8. A pharmaceutical composition comprising a polymorph according to claim 1 in admixture with at least one pharmaceutically acceptable excipient.

9. A topical pharmaceutical composition manufactured using a polymorph according to claim 4.

10. A topical pharmaceutical composition manufactured using a polymorph according to claim 5.

* * * * *

UNITED STATES PATENT AND TRADEMARK OFFICE
CERTIFICATE OF CORRECTION

PATENT NO. : 7,622,610 B2 Page 1 of 1
APPLICATION NO. : 11/354486
DATED : November 24, 2009
INVENTOR(S) : Rita Mayur Lodaya It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 859 days.

Signed and Sealed this

Fourteenth Day of December, 2010

David J. Kappos
*Director of the United States Patent and Trademark Office*